United States Patent [19]
Clynch et al.

[11] Patent Number: 5,432,703
[45] Date of Patent: Jul. 11, 1995

[54] LASER DIGITIZER SYSTEM FOR PRODUCING ORTHOTIC AND PROSTHETIC DEVICES

[75] Inventors: George Clynch; Jeffrey B. Allan, both of Calgary, Canada

[73] Assignee: Clynch Technologies, Inc., Alberta, Canada

[21] Appl. No.: 39,483

[22] Filed: Jun. 30, 1993

[51] Int. Cl.⁶ .................. G05B 19/42; A61F 2/76
[52] U.S. Cl. .................. 364/474.05; 364/474.24; 364/191; 264/40.1; 356/376; 425/142
[58] Field of Search .......... 364/474.05, 167.01, 364/468, 191, 473, 474.24; 356/376, 379, 380; 264/40.1; 425/142, 164, 174.4; 433/27, 29, 33

[56] References Cited

U.S. PATENT DOCUMENTS

| | | | |
|---|---|---|---|
| 4,575,805 | 3/1986 | Moermann et al. | 364/474.05 |
| 4,663,720 | 5/1987 | Duret et al. | 364/474.05 |
| 4,665,492 | 5/1987 | Masters | 364/468 |
| 4,821,200 | 4/1989 | Öberg | 364/474.24 |
| 5,092,022 | 3/1992 | Duret | 364/474.05 |

FOREIGN PATENT DOCUMENTS

| | | |
|---|---|---|
| 0040165 | 11/1981 | European Pat. Off. . |
| 0097001 | 12/1983 | European Pat. Off. . |
| 0251720 | 1/1988 | European Pat. Off. . |
| 3437483 | 4/1986 | Germany . |
| 3613096 | 10/1987 | Germany . |
| 2102597 | 2/1983 | United Kingdom . |
| 2188846 | 10/1987 | United Kingdom . |

Primary Examiner—Paul P. Gordon
Attorney, Agent, or Firm—Kerkam, Stowell, Kondracki & Clarke; John C. Kerins

[57] ABSTRACT

A system and method for producing a device, such as a prosthetic or orthodontic structure, is provided, having an inner surface for engagement with a portion of the human body. The system produces a more accurately fitting socket and involves a less time-consuming process with less discomfort to the patient. In the socket made from the mold, processed by the present system, the areas of enlargements provide areas of relief in the surface of the structure and the areas of reductions provide higher pressure areas in the areas in the surface.

38 Claims, 11 Drawing Sheets

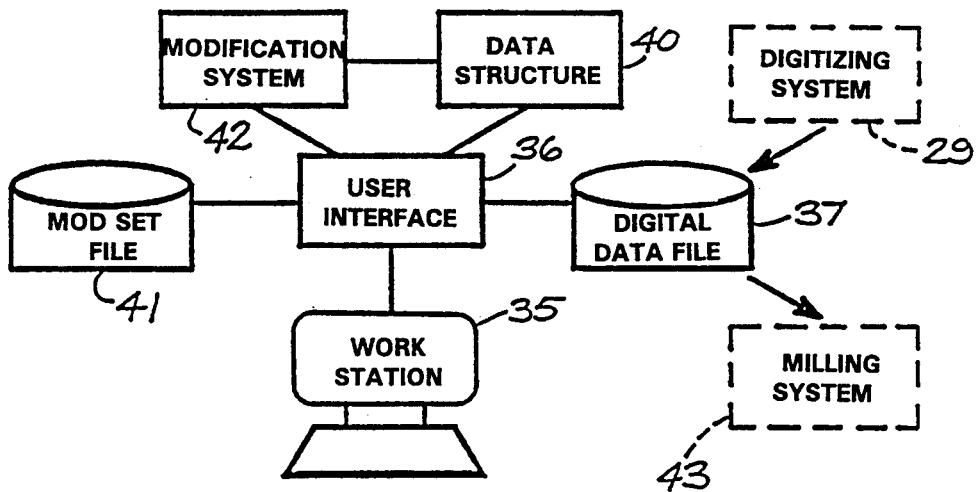
FIG. 4
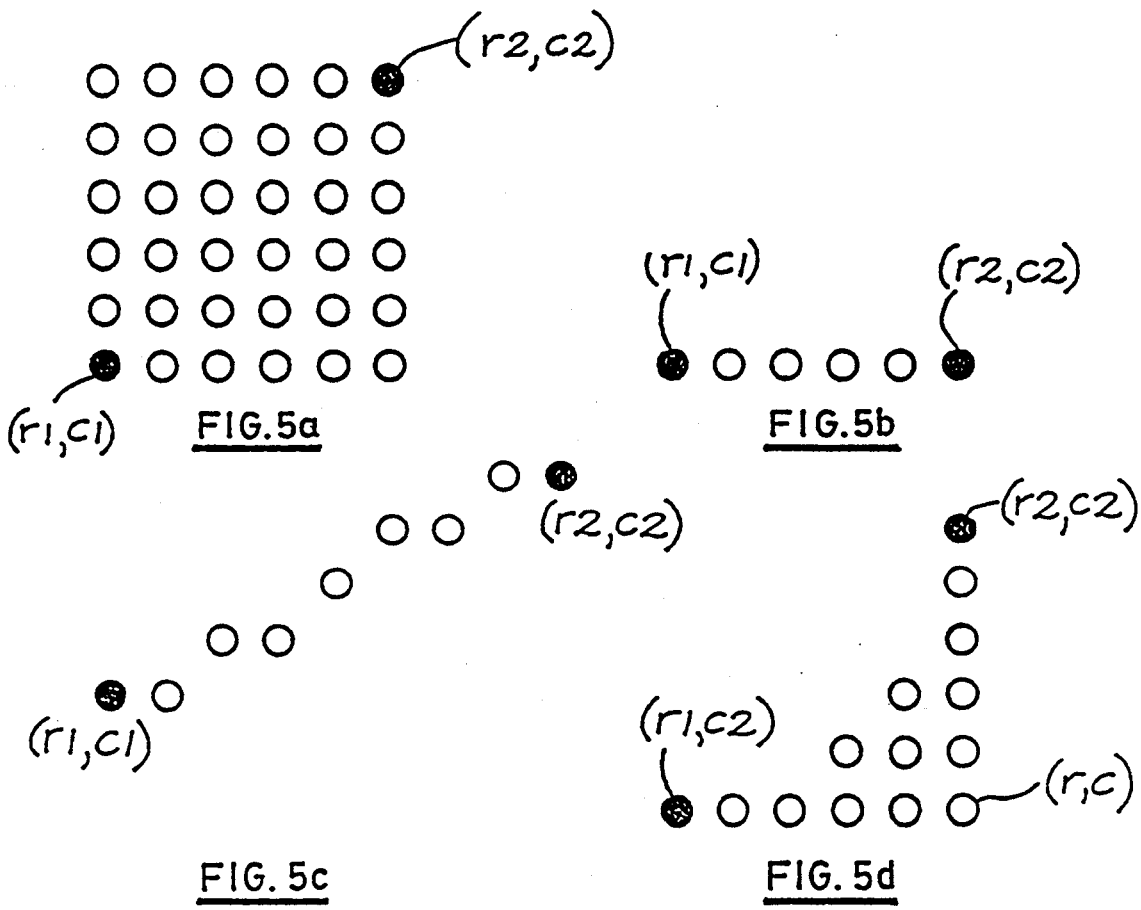
FIG. 5a   FIG. 5b
FIG. 5c   FIG. 5d

LASER DIGITIZER SYSTEM FOR PRODUCING ORTHOTIC AND PROSTHETIC DEVICES

This invention relates to a method and system for manufacturing prosthetic and orthotic type devices, and more particularly for producing an accurately shaped socket such as that for reception of a residual limb in a prosthetic structure.

The fit of a prosthetic socket is an important factor for comfort and function of the amputee. Currently, socket construction, as performed by prosthetists is an art form requiring many years of experience to master, and as the level of expertise varies considerably from prosthetist to prosthetist, there are many amputees fitted with devices having poorly fitted sockets.

The present conventional method of fitting a prosthetic device is by making a plaster cast of the patient's residual limb, commonly referred to as a stump. This process requires the fitting of the patient's residual limb with a special stocking, and with the patient standing in an apparatus that assists him in stabilizing his residual limb, or in a seated position, the plaster cast is made with a certain pressure applied to the residual limb by the prosthetist. The prosthetist then produces a positive mold from the plaster cast, and the positive mold is modified by reducing and building up specific areas of the mold. The inner shape of the socket must have variations in relation to the actual shape of the residual limb so that those areas of the residual limb that can bear weight will be weight bearing and those areas of the residual limb that cannot bear weight will have less contact with the interior of the prosthetic socket. The reduced areas on the positive mold will eventually translate to high pressure zones on the socket which will bear the weight of the body during all activities. The built-up areas will translate to low pressure zones in the socket which will bear minimal or no body weight. In the present conventional method, these manual modifications of the positive mold are done subjectively, but they are the key to an acceptable fit of the socket. As indicated above, the positive mold is made from plaster, usually a form of plaster different than the cast, the plaster forming the positive mold being poured into the plaster cast. In practice, a technician may be used, working under the supervision of a qualified prosthetist, to shape areas of the positive mold to account for the variations required to properly shape the interior of the prosthetic socket for fitting. Some areas are filed or otherwise shaved from the positive mold with basic tools such as files and sandpaper. Other areas of the positive mold are built up so as to provide a gap in the prosthetic socket to ensure that the sensitive areas of the residual limb do not bear as much or any weight. It can be seen that portions of the positive mold that are reduced will create a slightly smaller area in the prosthetic socket thereby making the fit tighter on those parts of the residual limb that can bear the weight. It is apparent, therefore, that the modifying of the positive mold is time consuming and expensive, and a large degree of the art and skill of a good prosthetist must be used in recognizing the pressure points of a residual limb so as to develop a comfortably fitting prosthetic device.

The socket which forms part of the prosthetic device is constructed preferably by laminating over the modified positive mold, and it therefore provides a negative image of the positive mold. The socket is normally in the form, therefore, of a continuous piece of laminate which has an interior shape the same as the positive mold as modified by the technician or prosthetist. The socket thus formed is fitted to the patient's residual limb to determine the accuracy of the fit and the socket is then usually attached to an appropriate prosthetic device. Most prosthetic devices are relatively standard and somewhat adjustable to the individual, and the greatest skill is required, therefore, in creating the prosthetic socket.

As long as the conventional method of forming the socket, which is a subjective process, is used, it will be difficult to establish the underlying principles for well fitting prosthetic sockets. In the event the socket does not provide a satisfactory fit, it may be possible to further modify the positive mold and to produce a second socket. However, depending on the magnitude of the required changes, it may be necessary to repeat the complete process starting from making the plaster cast, thus greatly adding to the cost of the prosthetic device. A normal production time from the beginning to the obtaining of a positive mold is about three and one half hours. Moreover, during the forming of the plaster cast on the residual limb, the patient is involved for a significant period of time which can cause some discomfort. Also a normal period for modification of the positive mold is about three hours. It has been realized, therefore, that if an objective quantitative process, could be developed for socket construction, underlying principles may be ascertained, and the result could be improved socket fit for many amputees.

In recent years, investigations have been conducted in relation to numerical quantifications of the construction of prosthetic sockets, particularly of the types used for below-knee amputations. A group, including Carl G. Saunders, et al. used mechanical devices to gather a sample set of measurements from a residual limb, and then selected a positive mold from a small library of computerized positive mold reference images. The measurements were used to scale and make modifications to the selected image, (see publication The CANFIT System; Shape Management Technology for Prosthetic and Orthotic Applications, Journal of Prosthetics and Orthotics, Vol 1, Number 3, pp 122–130). Then a numerically controlled milling machine was utilized to create a modified positive mold. Others have taken the approach of digitizing the inside of a negative cast with a mechanical digitizer to obtain a three dimensional numerical representation of the residual limb. The data thus obtained was modified according to some predetermined criteria, and a mold was then milled by way of an NC milling machine. Instead of digitizing the inside of the negative cast, Kurt Oberg has obtained a topographical image of the residual limb with an optical-laser digitizer and then followed a similar procedure for modifying the data by using predetermined criteria to eventually produce a mold (see U.S. Pat. No. 4,821,200, Apr. 11, 1989, entitled "Method and Apparatus for Manufacturing a Modified, Three Dimensional Reproduction of a Soft, Deformable Object" to Kurt Oberg). At least two major problems seem evident with the above described approaches. The first is that the identification of the bony landmarks or areas for modification has not been accurate. Secondly, the custom software developed for the modifications of the numerical data has generally not been sufficiently flexible to allow for proper modifications.

More specifically, while a number of attempts have been made to use the laser digital representation of a residual limb, there has been the major defect of not being capable of distinguishing sites for modification. The laser camera can only scan the exterior surface and cannot scan the underlying bone structure. Knowing both the exterior surface and the underlying bone structure is important for locating the various critical reference points of the residual limb. The critical reference points include the weight bearing and non-weight bearing areas of the residual limb. In addition to the weight bearing and non-weight bearing areas, other areas must be considered for functions of the socket (e.g. suspension or freedom of movement). In the above described conventional plaster method, the prosthetist palpates the bony areas of the residual limb to determine the exact location of critical areas. Each of the critical areas of the resulting positive plaster mold will be modified, such as by building up some or reducing others to accommodate the required functions of the residual limb. Therefore, one cannot make the appropriate modification to the digital image without knowing the locations and sizes of the critical reference points of the particular residual limb being fitted. The digital image does not lend itself to palpation to determine the underlying bone structure, and, of course, each patient's residual limb is quite unique given each patient's different size, weight, structural idiosyncracies and nature of their amputation.

It is an object of the present invention to provide a method and system of using quantitative information for constructing prosthetic sockets or similar devices wherein the areas of modification are accurately identified and adequately altered to provide an appropriate fit between the prosthetic socket and the residual limb.

According to the present invention, there is provided a system and a method for producing a structure for use in a prosthetic or orthotic device, or the like, which has an inner surface for direct engagement with a portion of the human body. The method includes the steps of defining the body portion and presenting an outer surface of the body portion for laser digitizing. The body portion is inspected and critical areas are identified on the outer surface by small non-reflective markings. The body portion is then scanned with a laser digitizer to produce a plurality of contour coordinates representing reflected points of the body portion contour along a plurality of closely spaced longitudinal lines read by the laser digitizer. The contour coordinates thus representing a digital image are stored as data including VOID-points produced by the non-reflective marks. The digital image is displayed graphically and basic modification areas are identified for the inner surface of the structure by way of the location of the VOID-points in the digital image. Selected points or vertices are identified within the basic modification area, and modified data is produced in relation to the selected vertices by moving the selected vertices for some basic modification areas in a positive direction relative to non-selected surrounding vertices to produce build-ups and by moving selected vertices of other basic modification areas in a negative direction relative to non-selected surrounding vertices to produce shrinkages. The modified data is used to produce code for controlling a cutting machine to produce a mold having a surface contoured to the likeness of the surface of the body portion but including areas of build-ups and areas of shrinkages. The structure which forms the device is then produced from the mold so that the areas of buildups provide areas of relief in the surface of the structure and the areas of shrinkages provide higher pressure areas in the surface.

More specifically, in the preparation of the portion of the body for digitizing with a laser camera, the portion of the body, such as a residual limb, is confined within a material which assumes the outer contour of the body portion. The material, which may be in the form of a stretchable stocking, thus provides the laser reflective surface, and, the location and the size of each area to be modified within the structure being made, such as a prosthetic socket, are indicated by a number of dots which, for example, may denote the outline of a bony prominence in the body portion.

While the moving of selected vertices of each basic modification area in a negative direction or in a positive direction may be done by moving all of the selected vertices the same amount, it is preferable to provide a blend range which surrounds the basic modification area so that the build-ups or shrinkages which result from the moved vertices in the basic modification areas do not have abrupt edges between them and the surrounding surface of the structure. Accordingly, the procedure of preparing modification data may also involve the movement of vertices surrounding the selected vertices in the basic modification area in the same positive or negative direction as the selected vertices, but by varying degrees, depending on their distances from the selected vertices so as to provide a blend range about the periphery of the basic modification area.

In the accompanying drawings, which illustrate an example of the present invention, FIG. 1 is a perspective view of a patient positioned for digitizing a residual limb;

FIG. 4 is a block diagram illustrating a structure of the CAD modification system;

Figure 8:
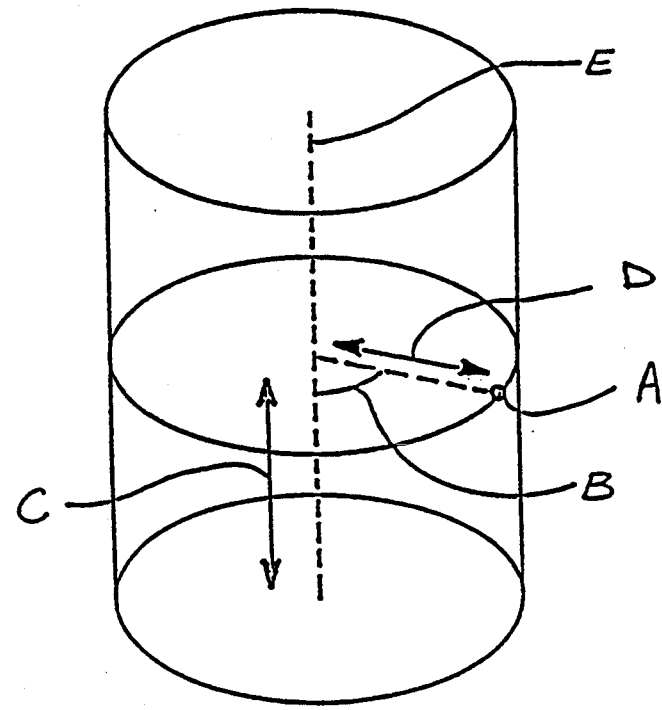
Figure 7:
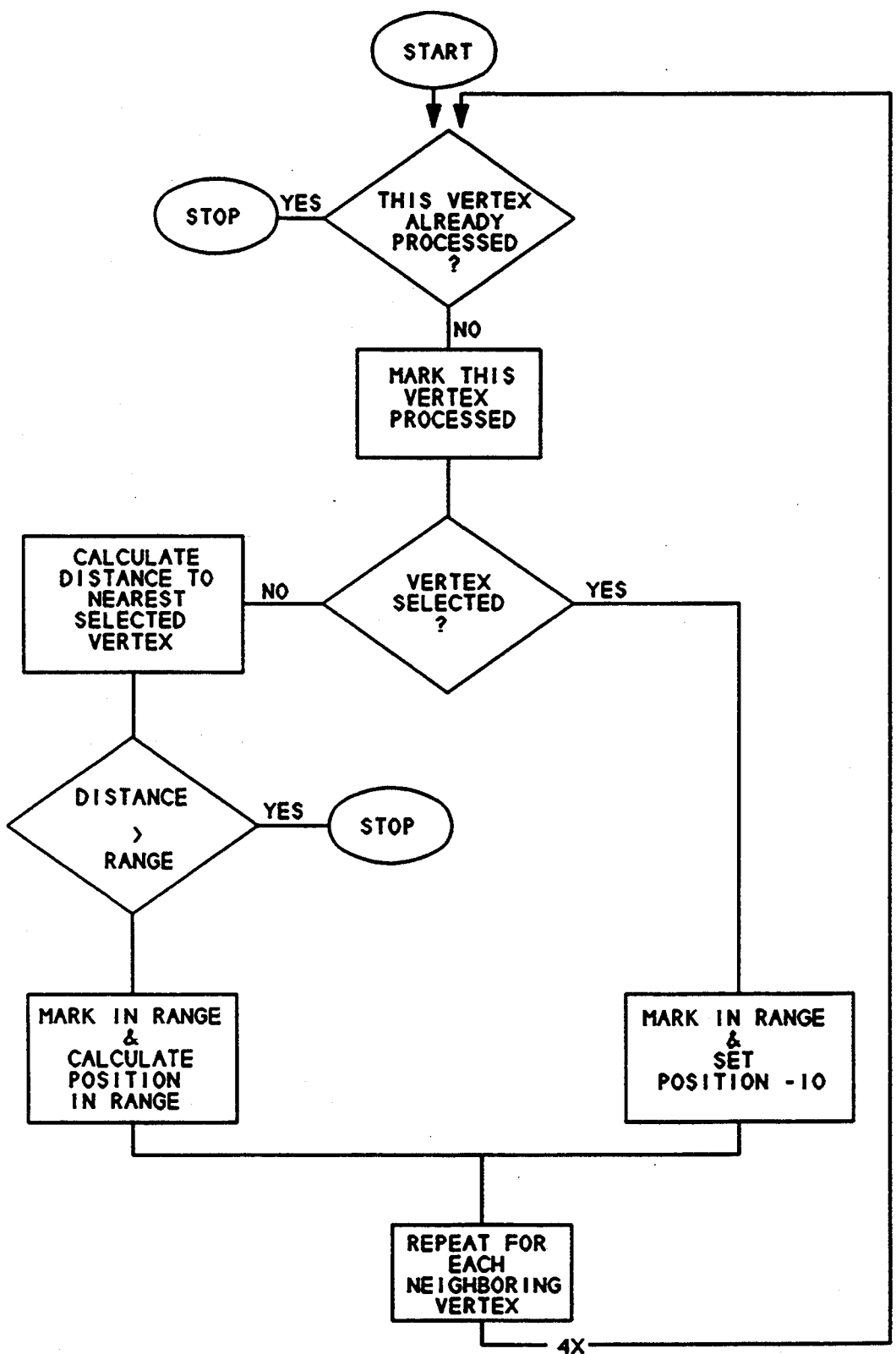
Figure 9:
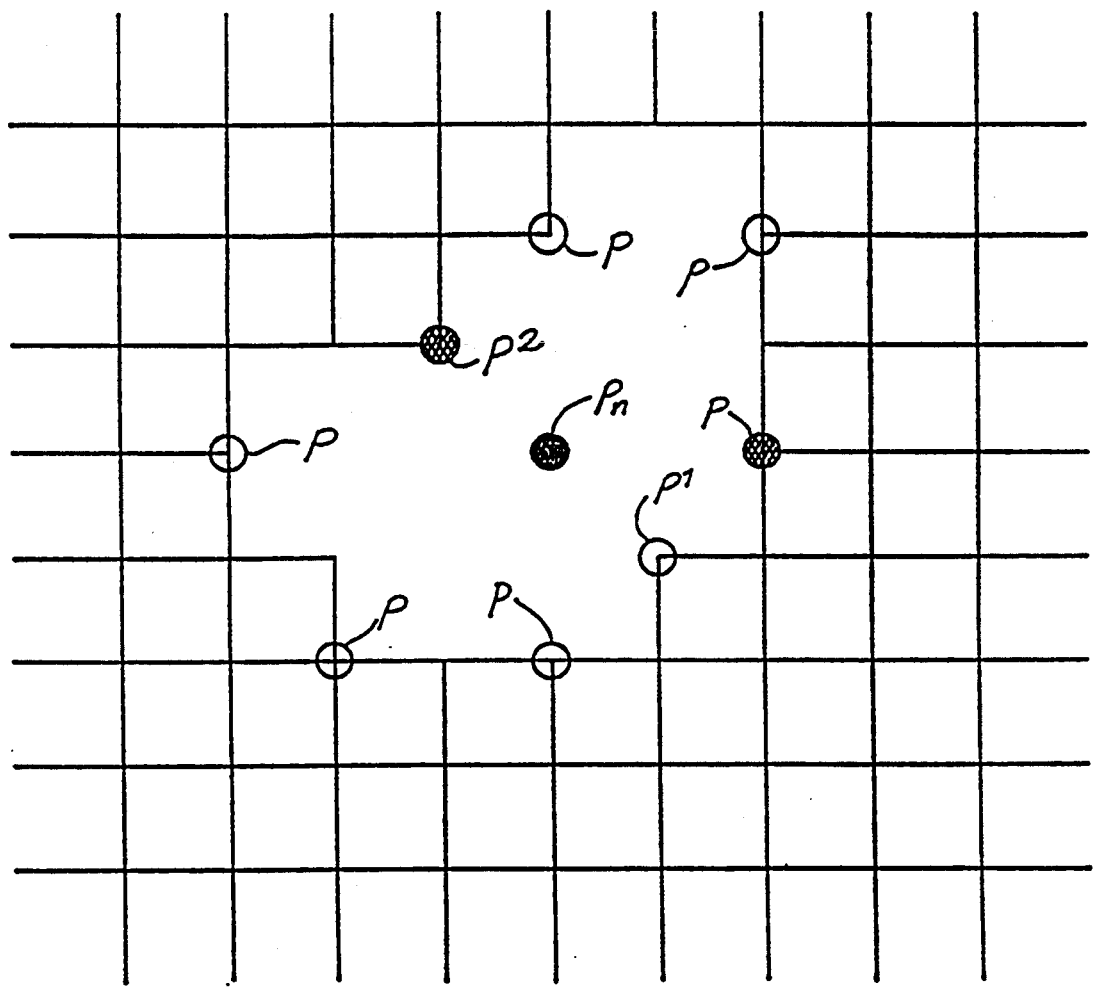
Figure 10:
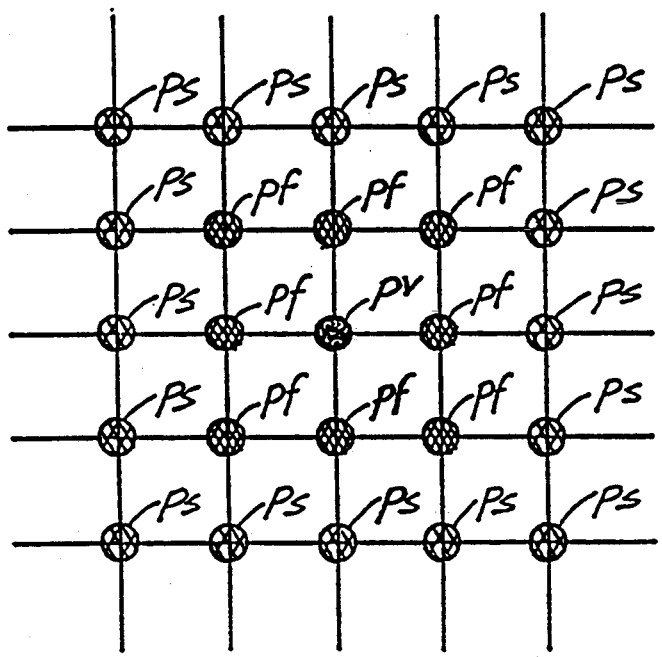
Figure 11:
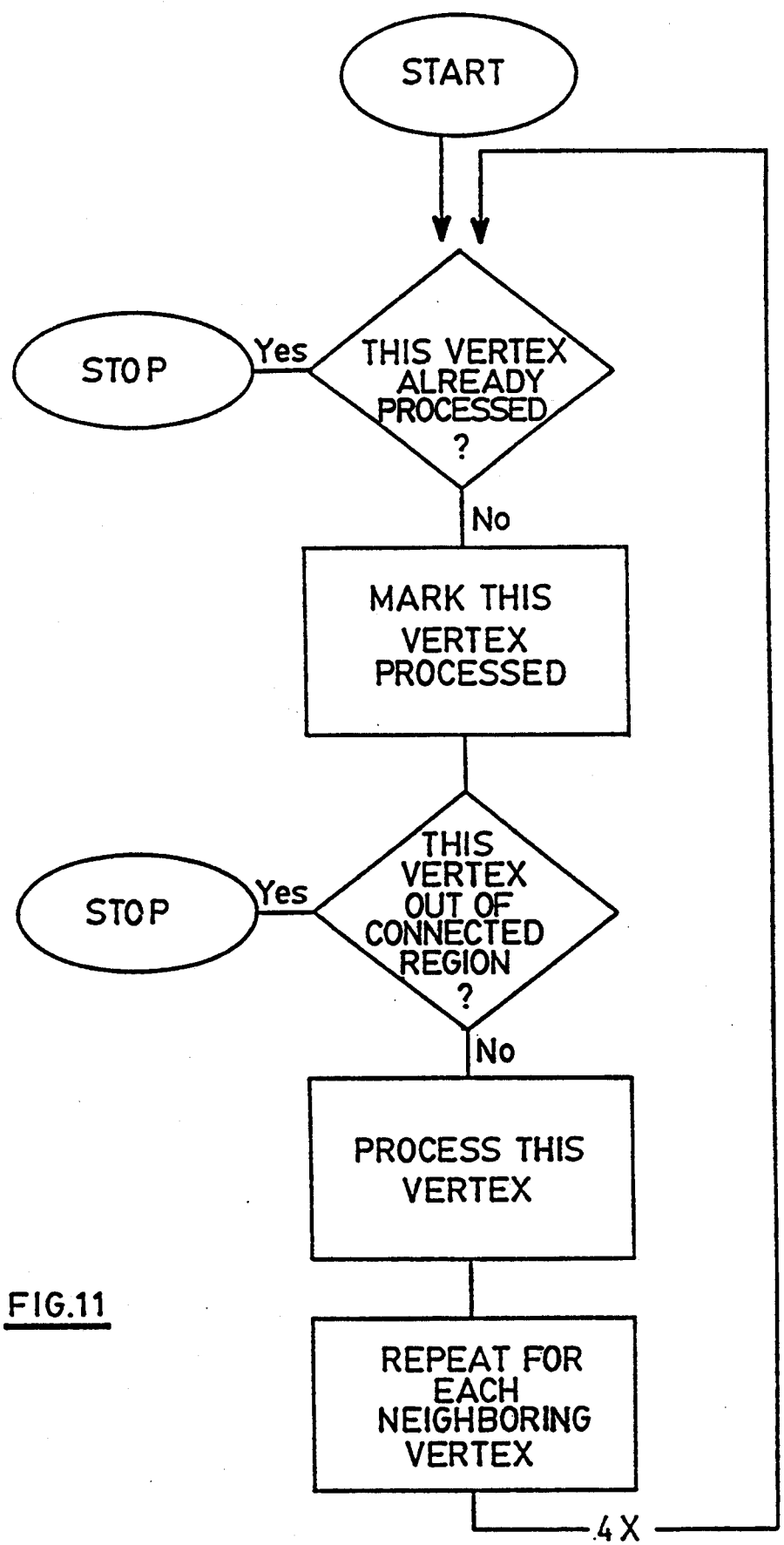
Figure 12:
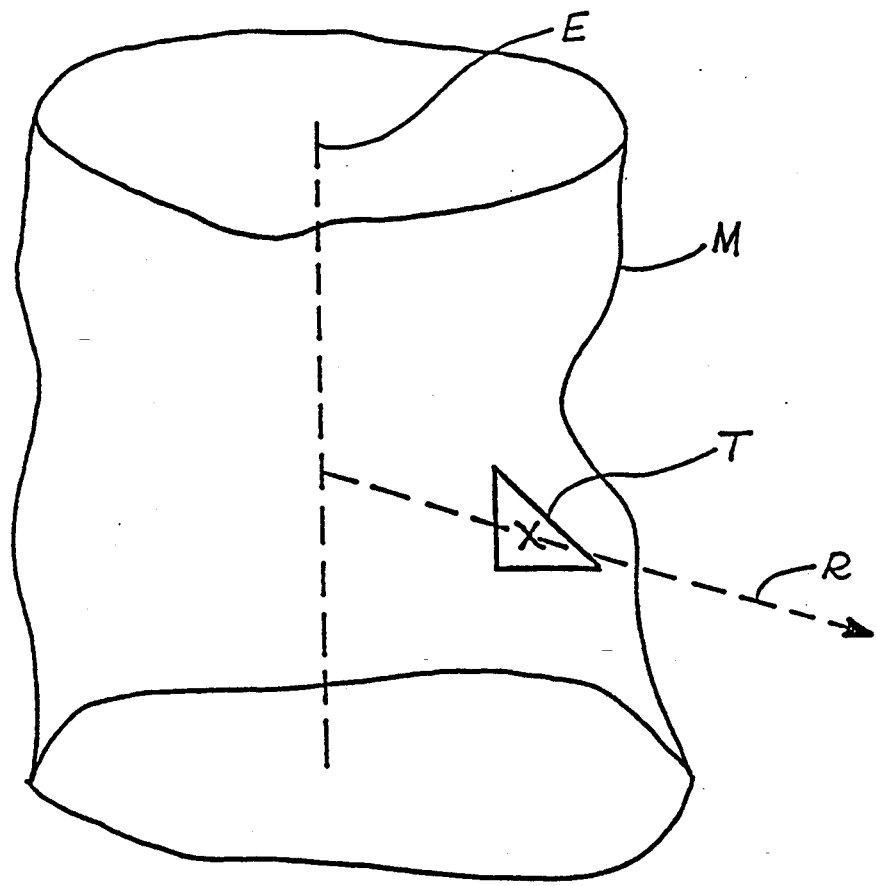
Figure 13:
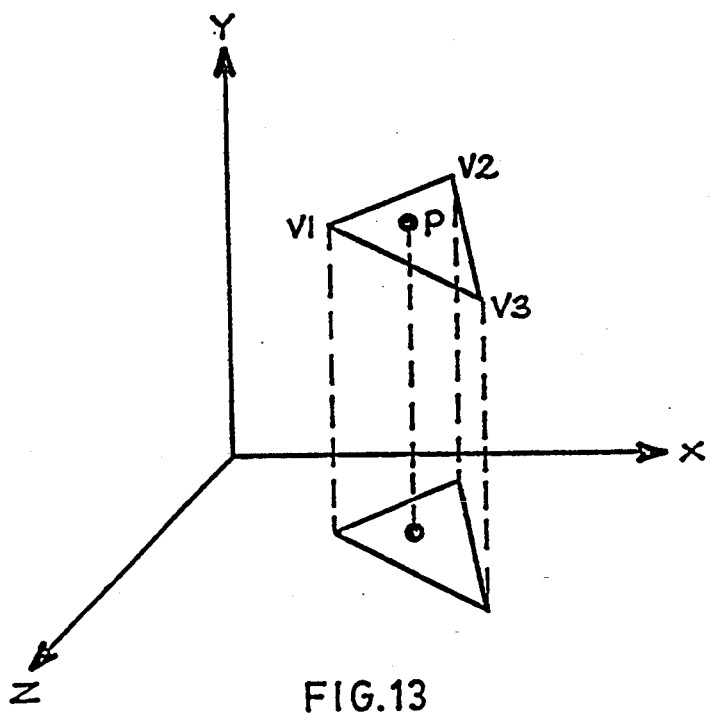
Figure 15:
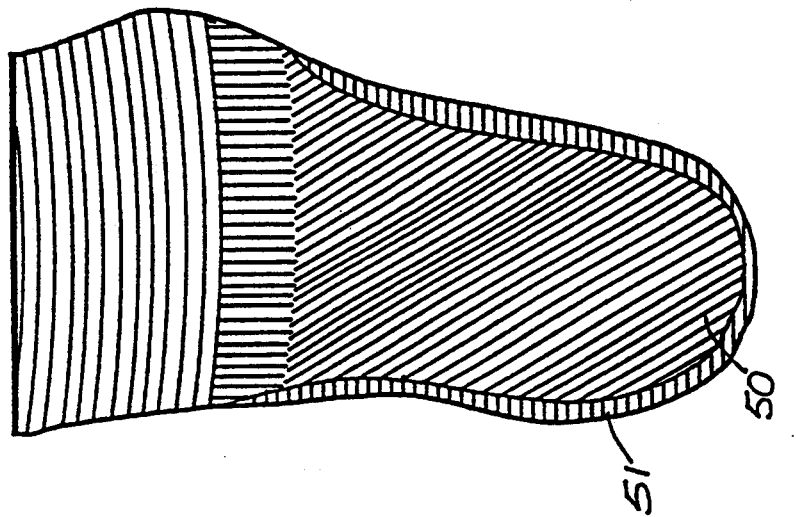
Figure 14:
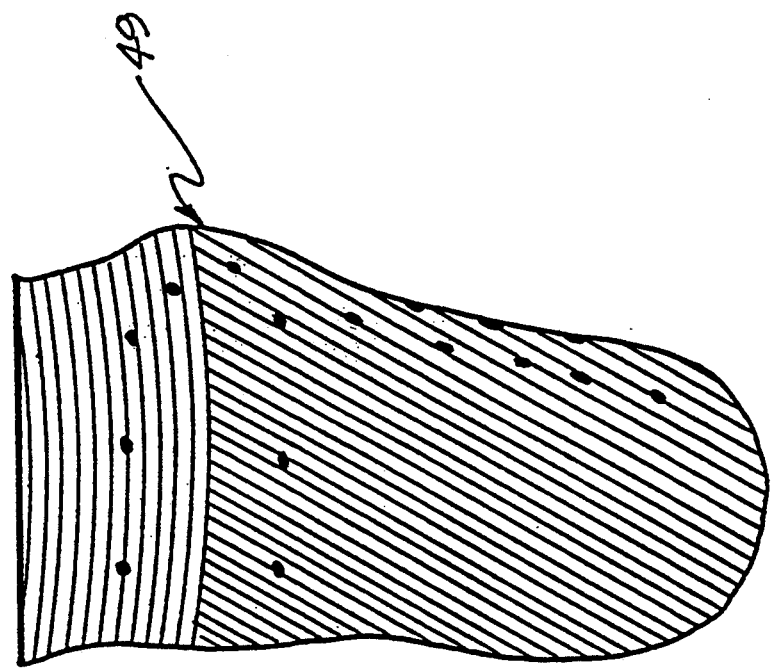
Figure 19:
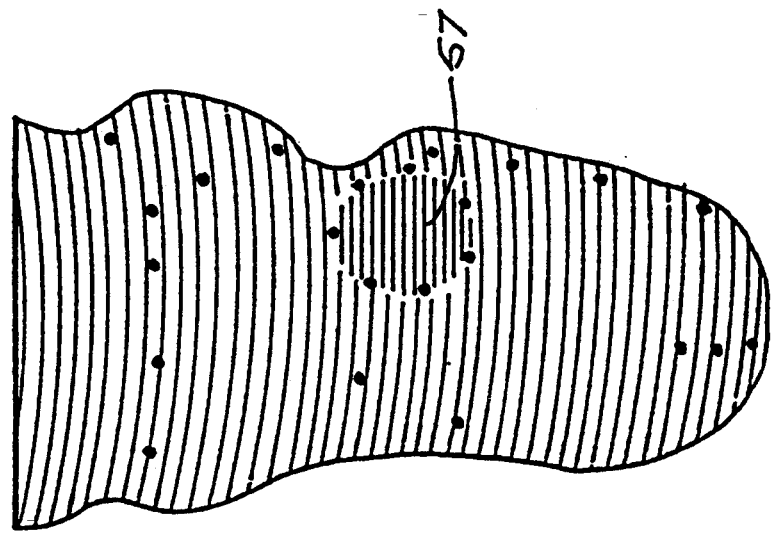
Figure 16:
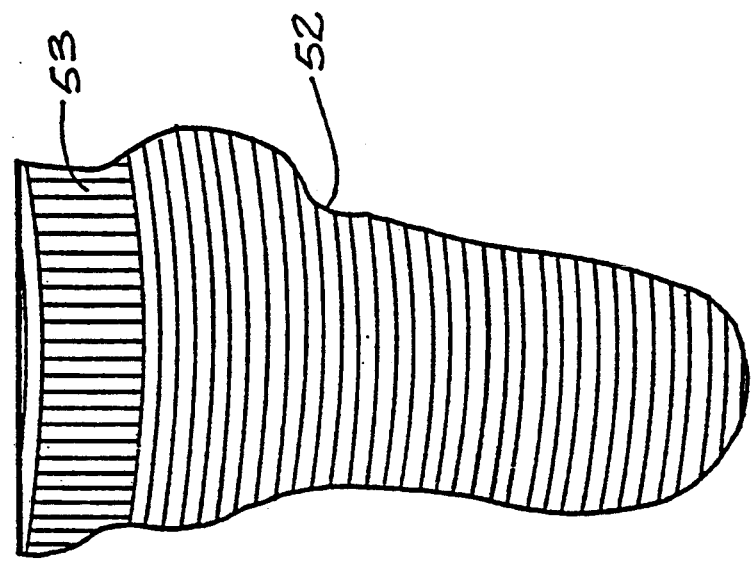
Figure 17:
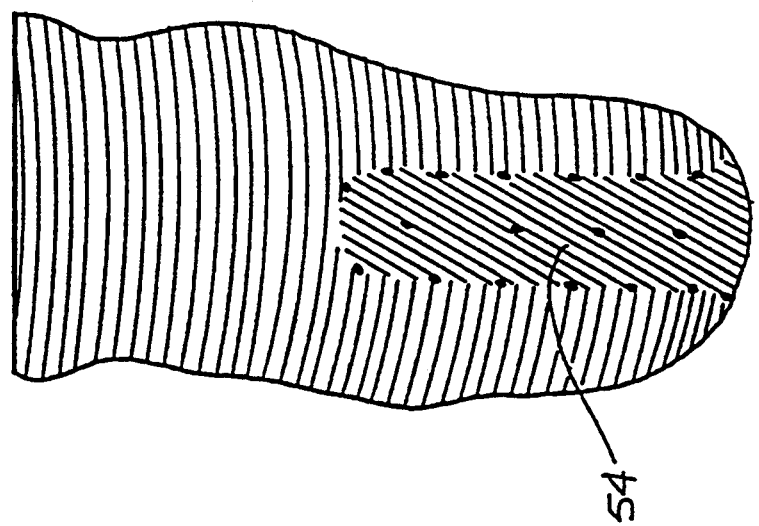
Figure 18:
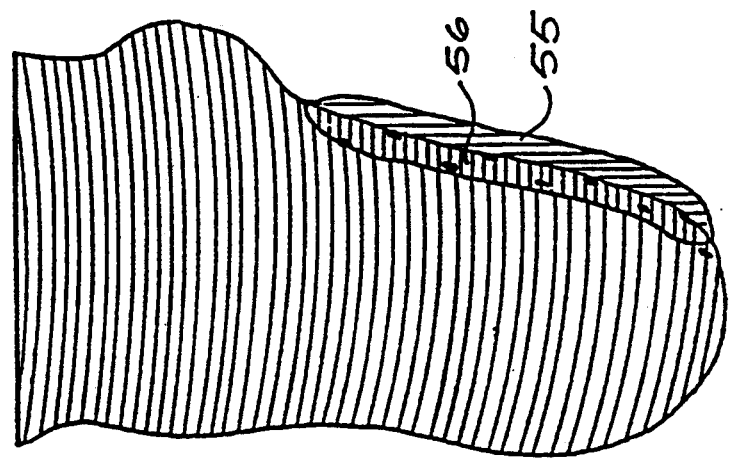

FIGS. 5a, 5b, 5c, and 5d are diagrams illustrating a set of vertex selection procedures within the software of the present invention;

FIGS. 6, 6a, 6b, 6c, and 6d are diagrams illustrating the procedure for blending shapes in the software of the present invention;

FIG. 7 is a flow diagram illustrating the blending range principle utilized in the software of the present invention;

FIG. 8 is a diagram illustrating the principle of cylindrical coordinates as used in the CAD software program of the present invention;

FIG. 9 is a diagram representing an interpolation procedure utilized in the software of the present invention;

FIG. 10 is a diagram illustrating a flood traversal procedure utilized in the software of the present invention;

FIG. 11 is a block flow diagram of the flood traversal principle utilized in the software of the present invention;

FIG. 12 is a diagram illustrating a process for converting Data Structure (DS) to a Digital Data File (DDF);

FIG. 13 is a diagram illustrating a projecting procedure used in the modified software;

FIG. 14 is a computer digital image of a lateral view of a residual limb showing a highlight of an area to be uniformly shrunk;

FIG. 15 is a computer digital image similar to that of FIG. 14 of a lateral view of a residual limb showing the final outcome of the uniform shrink;

FIG. 16 is a computer digital image showing the results of the final modification of the femoral condoyle of the residual limb image;

FIG. 17 is a computer digital image of a residual limb showing the front view of an area selected for creating the tibial crest relief area;

FIG. 18 is a computer digital image of the residual limb of FIG. 17 showing a side view of the final results of the modification to the tibial crest; and FIG. 19 is an image representing a side view of the residual limb as selected for modifying the lateral-anterior prominence of the tibial plateau.

Broadly the present invention resides in a method and system for producing a socket construction for a prosthetic device wherein an optical-laser digitizer is utilized to collect information which is representative of the outer shape of a residual limb and further includes an indication of the areas of the residual limb for which modification is required in the interior surface of the socket to take into account which parts of the residual limb are to carry weight, which are to be at least relatively free of pressure, and which parts have functional significance. The information thus collected is utilized by a computer with a custom computer aided design CAD software system to produce, according to input information supplied by an operator, altered numerical data. A program is then produced, using the altered numerical data for controlling an NC milling machine. The milling machine produces a positive mold which is the shape of the residual limb but includes modified areas, and a socket is constructed by forming a lamination over the positive mold.

Figure 1:
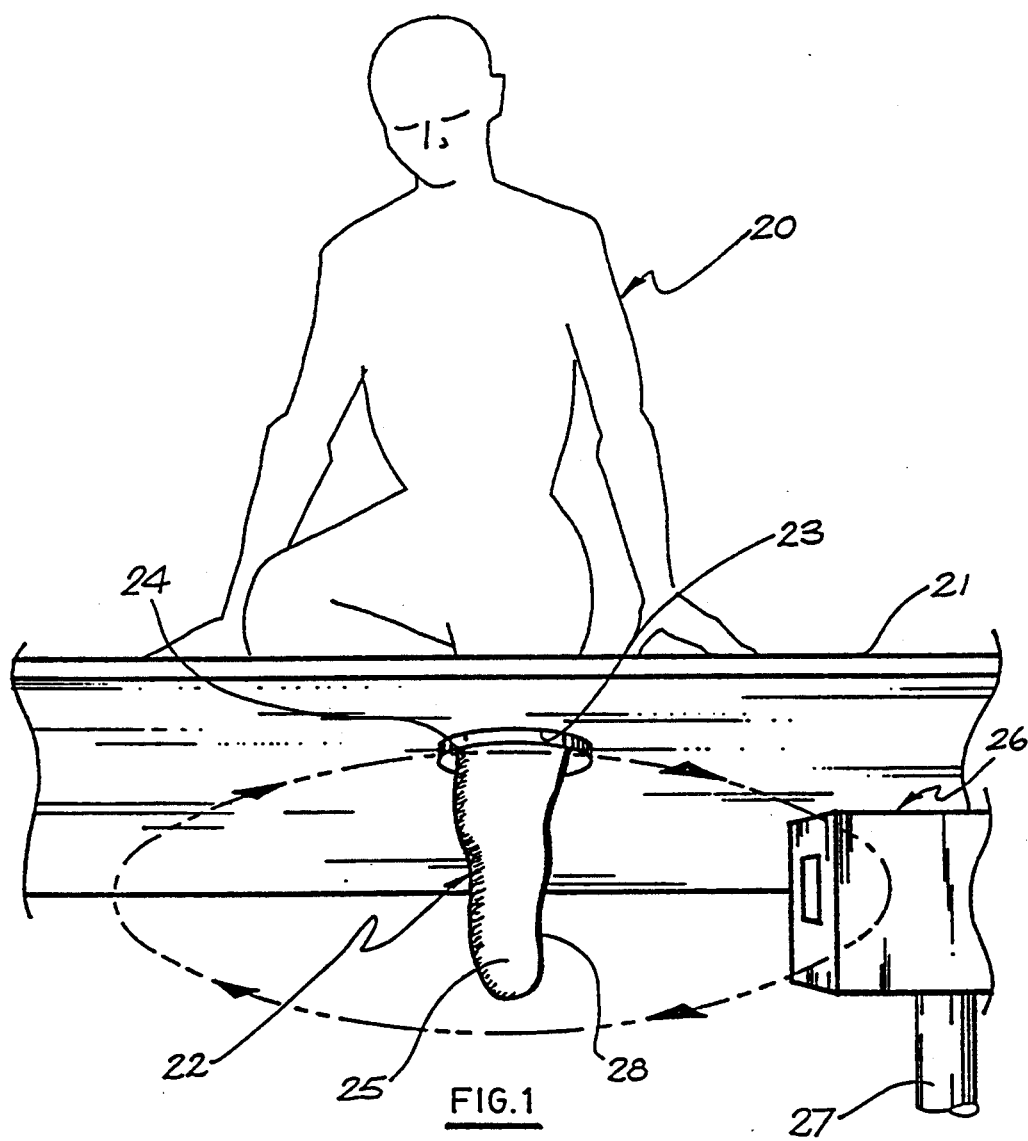

In FIG. 1 of the drawings, the patient, which is denoted by the reference character 20 is supported on a platform 21. The patient 20 is shown as a below-knee amputee, but it will be appreciated that the same principle as utilized in the invention as hereinafter described may also be used on other forms of amputations, as well as extremity orthotics, spinal orthotics, wheel chair seating, and orthopedic shoes.

In FIG. 1 a residual limb 22 of the patient projects through an opening 23 in the platform 21 and extends therebelow. The residual limb 22 is supported within a stretchable stocking 25 which is supported at the upper end thereof by a ring 24 held within the opening 23. The patient 20 is positioned so that a substantial portion of his weight is supported by way of the residual limb being located within the stocking 25. The stocking 25, which may be of a two-way stretchable type, thus bears a portion of the patient's weight through its securement to the platform 21 by way of the support ring 23. Although a platform structure has been shown, it is apparent that other support structures may be utilized, for example, to hold the patient in a more standing position so as to facilitate the patient placing more or less equal weight on the normal limb and on the residual limb contained within the stocking 25. It has been found that a more realistic shape of the residual limb can be measured if the residual limb is supported in a load bearing position within the stocking so that the stretchable stocking holds the fleshy tissues of the residual limb in a shape which the residual limb would normally assume when contained within the prosthetic socket being produced. As supported within the stocking, the residual limb projects below the lower surface of the platform with the longitudinal axis of the residual limb being substantially vertical.

A laser camera 26 is utilized to digitize the contours of the residual limb by effectively taking a large number of pictures each of which represent a relatively narrow vertical slice of the contours of the residual limb. As will be described in more detail below, the laser camera is part of a digitizing system 29 (FIG. 4) which collects numerical data describing the surface of the residual limb and specific locations for areas requiring modification. A low powered laser projects a line, which is shown at 28 in FIG. 1 along the longitudinal vertical length of the residual limb, and by way of triangulation through an optical lens, an optical sensor means is used to calculate the three dimensional coordinates of the points along the line 28. The laser camera, which is supported by means partially shown as 27 in FIG. 1 is carried on a turntable (not shown) which is located to permit rotation of the laser camera 26 about a vertical axis of the opening 23 in the platform. The laser camera may thus be indexed a fraction of a degree at a time about the longitudinal axis of the limb. For each indexing, the laser camera projects another line 28, and the process is repeated until a topographical mapping of the entire surface of the residual limb is obtained. The laser camera utilized in the present invention is a commercially available device which converts its laser images into digital form, and the digital representation thus provided is saved in the computer system. The digitizing and saving process is accomplished, therefore, by existing software for mapping the contours of 3-dimensional bodies.

The data resolution may be 256 data points per vertical line and 512 vertical lines in a 360° circumference. Therefore, there may be created 131,072 data coordinates of the residual limb. It has been found that a lower resolution of those data coordinates are often adequate for an accurate prosthetic fit. However, as many data coordinates as the prosthetist feels may be necessary given any particular patient can in fact be used. As the entire scanning process takes only approximately 15 seconds, it is possible for the patient to hold the residual limb uniformly positioned and it is not, therefore, a tedious or unpleasant procedure for the patient.

Figure 3:
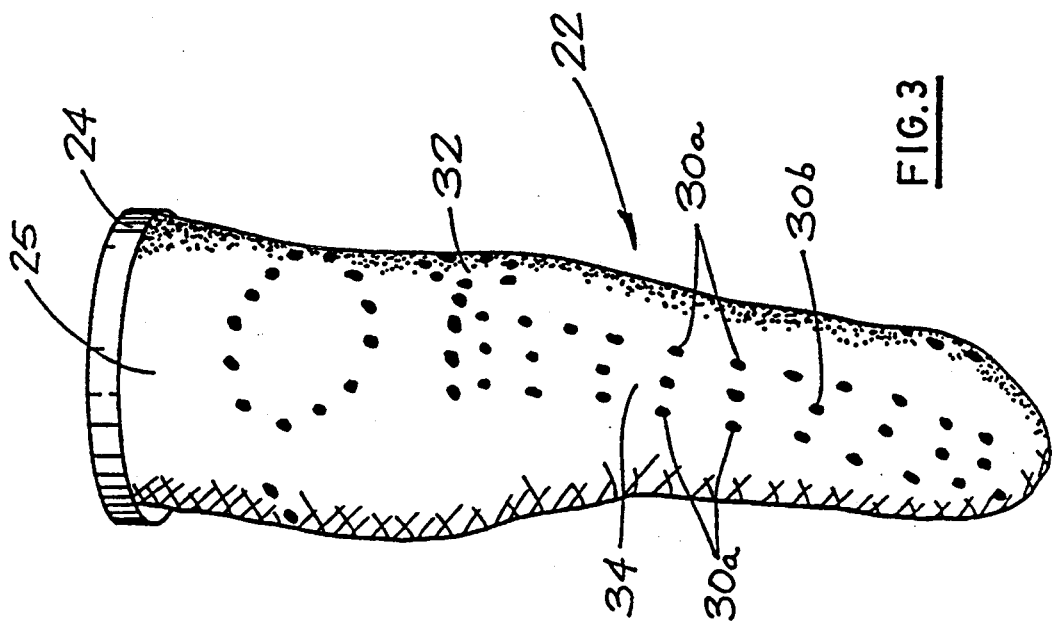
FIG. 3 is a front view of the residual limb of FIG. 2.
Figure 2:
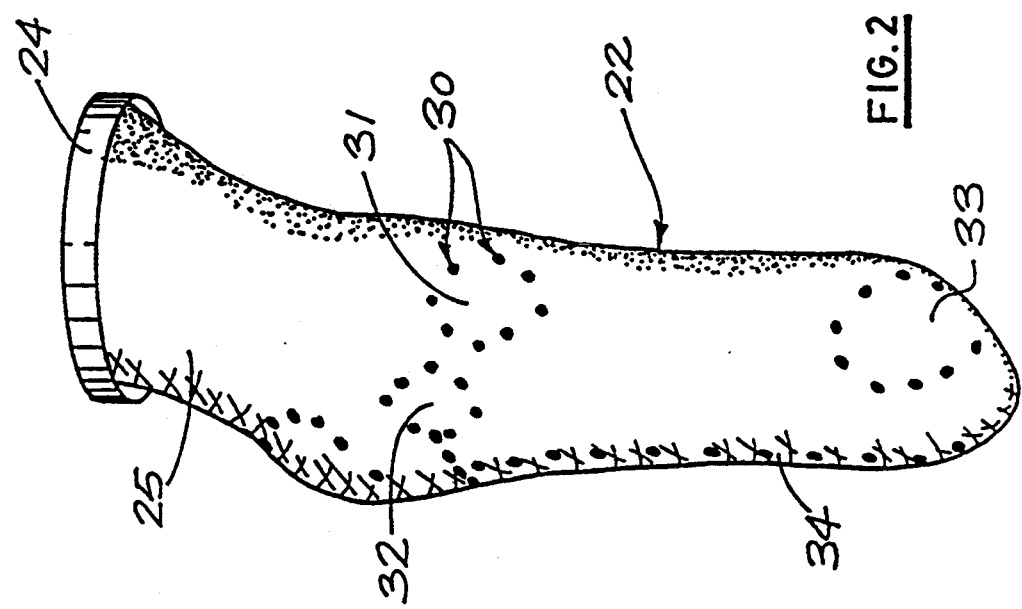
FIG. 2 is an enlarged side view of the residual limb of the patient as supported in a stretchable stocking.

Prior to the digitizing process, the prosthetist examines the limb as confined within the stocking 25, and by way of palpation determines the bony prominences of the residual limb. The range or lateral extent of a prominence is determined and marked by way of spaced dots on the stocking as best illustrated in FIGS. 2 and 3. The apex of a prominence within the spaced dots may also be marked on the stocking 25. The dots 30 (FIG. 2) are marked directly on the stocking by using a marker which will leave a spot which in effect absorbs the laser light, i.e. the spot is non-reflective of the laser light. While the stocking is of a material which will reflect the light so as to provide a reading to establish a series of coordinates, no reflection is received from the small area within the spot or dot 30 made by the prosthetist. By using a black waxy marking pencil the prosthetist creates a series of the black dots 30 utilizing his skill in determining the reference areas which normally form a number of critical areas. This is carried out by close physical inspection and contact with the physical limb. It has been found that many markers, such as indelible ink pen, crayons, black felt pens, black ball point pens do not provide a mark which is completely satisfactory in absorbing the laser sufficiently to prevent the laser camera from obtaining any reading from the small area occupied by the marking. Thus, while the digitizing process collects information establishing the coordinates representing the 3-dimensional outline of the residual limb, the points marked by the prosthetist leave gaps or VOID points in the collected coordinate data. A dense waxy marking pencil, such as one used for cosmetic eye liner, Which actually provides a small coating in the dot area on the stocking, has proven satisfactory. For reasons which will become apparent below, dots are used because solid lines produce too many VOID vertices, the positions of which must be estimated by the CAD software.

In FIG. 2 there can be readily seen one set of dots 30 which outline or provide the range for the head of the fibula 31, while another set of markings or dots outline the lateral-anterior prominence of the tibial plateau 32. A third set of marks outlines the area 33 occupied by the distal end of the fibula. In the front view of the residual limb shown in FIG. 3, the two outer series of dots 30a, 30a provide the outline of the tibial crest 34 while the center series of lines 30b denote the most prominent portion of the tibial crest.

The total software used in the system of the present invention includes a specially developed CAD System program which enables the prosthetist to make unique changes to the data in the form of the 3-dimensional coordinates collected by way of the laser camera. The system further Uses some software programs which are commercially available. The system includes a digitizer control program which is part of the laser camera and is used in collecting the digital data in what is known as cylindrical mathematical coordinates. This data permits the production of the graphical 3-dimensional representation of the data at the graphics terminal. The system also includes a specially developed software program which converts the manipulated digital image data file into what is known as G-code. A commercially available G-code transmission software program operates a cutting machine, usually a numerically controlled (NC) milling machine and is capable of reading the G-code. As indicated above, the system includes a unique CAD software program which permits the kinds of manipulation to the data collected for the CAD System suitable for use in the practice of prosthetics, and other applications of the invention.

In the modified form, the software enables the prosthetist to make quantifiable changes. For example, the prosthetist can reduce the entire volume by 3%. The volume can be reduced by exactly 3%, for example, and that exact change from the original is stored Another feature of the CAD software is that when a reduction or an enlargement to and area is made it is blended into the surrounding surface i to avoid producing an abrupt edge. In other words, there is an abrupt change between the area which has been moved to a reduced or to an enlarged position, and the software then automatically calculates and changes the contour from the abrupt or sharp change to a gradual contour within a certain range, which range is inputted by the prosthetist.

The CAD software is also capable of creating a uniform 360° change, i.e. a uniform enlargement or a uniform shrink of the limb image or any part of it. This is used, for example, to create the necessary uniform shrink of the limb distal to the patella.

The uniform shrink capability can also be used for refit. During the first year of an amputation of a patient, frequently two or three refits, or even up to six refits, may be required due to atrophy of parts of the residual limb. Unlike the conventional plaster method, where the prosthetist must recast the residual limb to produce a new socket for each refit, the present system permits the immediate production of new 3-dimensional coordinates in the stored data to compensate for the atrophy. The system allows the coordinates to be modified to provide a uniform 360° shrink and then a uniform enlargement of the bony areas that do not atrophy by the same quantifiable amount that the non-bony areas have shrunk.

The CAD software is capable of rotating the image of the residual limb 360°, translating the image up and down and side to side, zooming in and zooming out a particular area, prompting the prosthetist with respect to the modifications of each critical area, and showing both the original limb and the modified limb as an overlay of one another.

Colour coding can be incorporated into the program so as to illustrate in one colour the shape of the unmodified residual limb and in a different colour a modified portion, for example, which will provide for the expanded area to receive a bony prominence in the final socket.

Because changes will be made in relation to the reference points Which are known because of the gaps or VOID points in the data of the digital image created by the black dots applied by the prosthetist to the stocking, the software displays the reference points in a different colour. The software may collect data and generate a data base of the degree of modification of the critical areas. This data may be used to assist the prosthetist in accelerating the modification process of future residual limb images. The software is also capable of doing a rough first modification of the residual limb image based on averaging the proportion and range of changes made to previous data sets. The software can do this because the key to making these changes are provided in the collected information by way of the reference points. The prosthetist may then perform fine tuning modification to the residual limb image. In this manner, the software in effect is helping the prosthetist with modification decisions yet also allowing for the specific intervention by the prosthetist.

More specifically, the software system used by the invention to modify the residual limb data is illustrated in FIG. 4. As indicated, the system uses a unique basic CAD System and may be described as having the following sections: the User Interface (UIF), the Data Structure (DS), the Modification System (MS) and Algorithms and Formulas. FIG. 4 illustrates the relationship among the following major components of the system: Workstation 35, User Interface (UIF) 36, Digital Data File (DDF) 37, Data Structure (DS) 40, Mod Set File 41 and Modification System (MS) 42.

The Workstation 35 displays the data structure graphically and interacts with the operator using text-based and graphics-based interaction. The User Interface (UIF) 36 reads the Digital Data File (DDF) 37 produced by the digitizing system and stores it in the Data Structure (DS) 40. The UIF 36 displays the DS 40 graphically on the workstation screen. The UIF 36 reads a set of modification directives (a Mod Set) from the Mod Set File 41.

The modifications are applied to the DS 40 by the Modification System (MS) 42 and the UIF 36 updates the display to reflect the modifications. The UIF 36 allows the operator to interactively edit the Mod Set which in turn results in changes until the modified DS is correct. The UIF 36 stores the Mod Set in a new Mod Set File 41 and stores the DS in a new DDF 37 which is used as input to the NC milling system 43.

The UIF 36 provides the control interface for the operator. It displays the DS 40 graphically on the workstation, reads and writes Digital Data Files and Mod Set Files, constructs the DS 40, and controls the MS 42 which modifies the DS 40. In the current implementation of the invention the UIF 36 uses three windows and six sets of menus on a bit-mapped workstation screen: one window for displaying messages to the operator, another for editing the mod Set, and the third for displaying the DS and interacting with it graphically. The menus and interaction window are used by the UIF 36 to conduct a dialogue with the operator allowing the following operations to be carried out:

Specify which Digital Data File to read and use to build the DS;

Specify which Mod Set File to read and store internally;

List the Mod Set and select a modification to edit;

Edit the parameters of a modification;

Update the graphical window to reflect the DS after applying the edited modification;

Repeat the process of selecting and editing modifications Until the resulting form of the data structure is correct;

Save the edited Mod Set to a Mod Set File.

Save the modified DS to a new Digital Data File suitable as input to the digital milling system; and Quit the CAD System.

The graphical interaction window displays the DS graphically as a "wire frame" by drawing a connecting line between each vertex captured by the digitizing system and its immediate; neighbors above, below, to the left, and to the right. The points in the DS are converted from the three-dimensional (3D) coordinate system in which they are stored onto the two-dimensional (2D) display screen of the workstation. The graphical interaction window is used in conjunction with a 2D pointing device (for example a mouse, track-ball, or touch sensitive screen) to select vertices and groups of vertices of the DS. The operator is able to modify the 3D point of view and direction of view to obtain any perspective of the DS desired. The graphical interaction window makes use of different colours to display the DS For example, colour is used to distinguish those parts of the DS which have been selected for modification.

The CAD system (FIG. 4) stores the information contained in the Digital Data File in a special purpose Data Structure (DS). The DS represents each point in the DDF with a "vertex record" which contains the following information:

Current position of the vertex (3D coordinate);

Original position of the vertex (3D coordinate);

Selected (binary flag) True when this vertex has been selected;

In range (binary flag) True when this vertex is in the bending range; and

Position value (real number) Position within the bending range.

The vertex records are stored in a 2D array of vertices. Each column of the array represents a vertical column (longitude) of the Digital Data File. Each row of the array represents a horizontal row (latitude) of the Digital Data File.

The method used to modify the DS consists of selecting a set of Vertices to move and specifying a distance and 3D direction to move them. A blending range of vertices surrounding the selected ones can be specified. Vertices in the blending range will move as required to blend the modification with the surrounding surface. A blending shape is specified which will produce the sort of blending desired. Each of these steps is described in considerably more detail below.

The software is designed to provide a menu on the terminal screen of the Workstation 35, and for a residual limb of a below-knee amputee the menu may read as follows:

| Selection 0. | "uniform shrink" |
| --- | --- |
| Selection 1. | "patella tendon" |
| Selection 2. | "femoral condyle" |
| Selection 3. | "tibial crest" |
| Selection 4. | "head of the fibula" |
| Selection 5. | "lateral-anterior prominence of the tibial plateau" |
| Selection 6. | "distal end of the fibula" |
| Selection 7. | "distal end extension" |
| Selection 8. | "posterior wall extension" |

By choosing one of the selections the prosthetist may commence modifying the data collected by the digitizing process. There is shown in FIG. 14 the computer digital image 49 of an example residual limb. On a coloured screen, the gaps or VOID points in the data created by the black dots on the stocking show up as blue dots. By selecting 0 the prosthetist receives views of the area selected for the uniform shrink. On giving the information for the uniform shrink, colour shaded areas 51 may indicate the difference between the original contour of the residual limb (FIG. 15) and the area 50 remaining after the shrink.

The operator may then continue by selecting 1 which is the area for the patella tendon bar. In this area, the socket is to be reduced, and the modification results in an indent in the image as illustrated at 52 in FIG. 16. Next the area of the femoral condyle is modified which also requires a reduced area, and the shaded area 53 in FIG. 16 shows the manner in which a differently coloured area would indicate the final modification of the femoral condyle. The area for modifying the tibial crest is then selected, and as is apparent from FIG. 17, the dots added to the sock define the outer range of the area within the socket to be relieved so as to avoid pressure on the portion of the limb in the area of the leg commonly known as the shin bone. The dots which show up on the screen image within the outer range indicate the highest ridge or crest of this bone. The shaded area 54 shows on the screen in a yellow colour, for example, indicating the area to be modified. The prosthetist may indicate, for example, that this area is to be displaced by 2 cm and the software described above moves the coordinates to provide the increased displacement area and also to blend it into the surrounding area. FIG. 18 shows the modification to the tibial crest area, with the shaded area 55 indicating the added portion while the shaded area 56 indicates the area as present without modification.

Next, the prosthetist may move on to the area to be increased for the head of the fibula and this area is modified in a manner similar to that described in connection with the tibial crest, except that this area, rather than being elongated, is of relatively circular area. The shape to be modified for the lateral-anterior prominence of the tibial plateau area is similar, and this is illustrated as area 57 in FIG. 19. As in the cases of all of the other areas, the coordinates of the location to be modified are accurately positioned in view of the provision of the dots on the image by the VOID points included in the digitized data because of the black markings placed on the stocking at the time of digitizing. In FIG. 19, the image includes the previous modifications described above, and the area 57 is shown as a yellow area, i.e. an area to be modified. Following modification of the lateral-anterior prominence of the tibial plateau area, the prosthetist may modify the area to be enlarged for the distal end of the fibula. This is then followed by modification of the distal end extension and finally the posterior wall extension which is provided in the socket with an expanded area. It will be realized from the more detailed description of the functioning of the unique software involved as set out below, it is possible for the prosthetist to make any additional modifications deemed necessary for the particular residual limb involved.

When the modifications have been made the software is then utilized to provide information to another program which generates code to operate an NC milling machine which cuts out the positive mold. Typically a soft material is used as the milling workpiece to be cut.

The code required for the milling machine is known as variable block format, or G-code. The code is composed of instructions used to control the movement, speed and feed rate of the milling machine cutting tool. In general, the cutting tool is made to follow a path in a similar fashion to that in which the residual limb was originally digitized. That is to say, the cutting tool cuts at longitudinal path on the workpiece describing one longitudinal contour of the modified positive mold. The workpiece is then rotated by a small amount about its longitudinal axis. The amount that the workpiece is rotated can be from a fraction of a degree to any multiple thereof, depending on the resolution required. After the rotation, the tool cuts a second longitudinal path along the workpiece. This cutting/rotation cycle continues until the modified positive mold is completely formed.

The data describing the surface of the modified positive mold is used as a reference for the program which generates the milling code (G-code). In order for the positive mold to be cut accurately, however, it is necessary to take into account the complex geometries concerning the shape and size of the cutting tool and the shape of the positive mold surface. For example, simple generating code which would cause the tip of the cutting tool to move directly to a given data point may cause several adjacent data points to be 'gouged' away. In order to prevent this, the shape and size of the cutting tool as well as the geometry and proximity of the intended data point and adjacent data points must be accounted for. This is done through algorithms in the Code generating program.

It should be noted here that the fact that the milling paths are Somewhat similar to the method in which the data was collected was mostly for the sake of simplicity. What is most important is that the accuracy of the resulting formed positive mold is preserved through careful consideration of the geometries of the cutting tool, cutting tool path and positive mold.

Once the code has been generated and written to a data file, it is transmitted to the milling machine controller using commercially available software.

Once formed, the socket is fitted, and if it is apparent that further modifications are required, the type of modifications may be noted and then carried out after again selecting the appropriate area on the above-described menu. Having made the modifications further required as a result of the fitting, a further positive mold is produced and a new socket is then formed on the new positive mold.

As previously described, the information produced for the final fitting may be stored, and if a new socket is subsequently required, due to various reasons, such as atrophy, the information can then be recovered and modified, for example, to provide an additional uniform shrink while taking into account the fact that with the further shrink, additional expansion may be required in the bony prominent areas.

The process of modification described generally above is carried out by specifying and altering a set of parameters for each modification. The set of parameters of each modification (e.g. uniform shrink, tibial crest) differ lightly from one modification to another. Generally, though, each modification has parameters which describe:

the name of the modification
the set of vertices which are selected
the size of the blending range
the shape of the blending range
the direction in which selected vertices and vertices in the blending range are moved
the distance by which these vertices are moved Each modification may use slightly different parameters to describe each of the items listed above.

The name of the modification is always described as a string of characters.

The set of vertices which are selected can be described in either of two ways:

1) as a rectangle shaped region—in which case the parameters are the coordinate of the center of the bottom of the rectangle, the width of the rectangle, and height of the rectangle;
2) as a chain of vertices—in which case the parameters are a list of any number of vertex coordinates, each pair of which will be connected by a straight line of selected vertices. In the first case, there may also be another group of parameters which describe the radius of curvature used to round each of the corners of the rectangle of selected vertices.

The size of the blending range can be specified by one, two, or four parameters which describe the width of the blending range in every direction around the set of selected vertices. When only one parameter is used, it is the width of the blending range in all directions. When two parameters are used, they are the widths of the blending range in the vertical and horizontal directions respectively. When four parameters are used, they are the widths of the blending range in each of the four directions: up, down, left, and right.

The shape of the blending range is always represented by one parameter which names one of the available blending range shapes. In the current implementation, the available blending range shapes are: square, triangular, round, and cusp.

The direction in which selected vertices and vertices in the blending range are moved is always represented by a single parameter which names one of the available directions. In the current implementation, the available directions are: normal to the surface of the object, normal to the surface of the object but constrained to move in a horizontal plane, and vertical.

The distance by which selected vertices and vertices in the blending range are moved is always represented by a single parameter which specifies the distance by which they are moved.

The following example lists the parameters for the modification which is applied to the crest of the tibia, together with some typical values for the parameters.

| PARAMETER | TYPICAL VALUE |
|---|---|
| Name | "Tibial Crest" |
| Chain | (104,456), (94,456), (82,456), (68,460), (56,462), (40,464) |
| Blending Range Width | 2.0 |
| Blending Range Shape | Round |
| Direction | Normal |
| Distance | 0.78 |

Since the set of parameters which comprise a modification can be altered, it is possible to create a parameter list for any modification that can be imagined.

In this way, new modifications can be added to a set of modifications if necessary to accomplish a comfortable fit for a patient whose limb is irregular in shape or proportion.

Referring to FIG. 5, vertices are selected textually (as row/column DS coordinates) or graphically (using the 2D pointing device) through the UIF. They can be selected individually or in groups. Groups can take any shape: e.g. a rectangle (FIG. 5a), a single row (FIG. 5b), a diagonal line (FIG. 5a) or a corner (FIG. 5a) as shown. The UIF ensures that groups of selected vertices are adjacent to one another since they represent a region which the operator wishes to modify.

All selected vertices are moved by the same distance. The distance is specified textually through the UIF. Positive distances cause build-ups or extensions to the DS which provide relief for sensitive areas. Negative distances cause depressions or shrinkages to the DS which provide greater pressure for weight bearing areas. The direction in which selected vertices move is specified textually through the UIF. Although the direction can be any 3D vector, it is generally expressed relative to the DS (e.g. normal to the surface represented by the DS). Three common directions are: distally, posteriorly, and normal to the surface represented by the DS. All selected vertices do not necessarily move in the same 3D direction. For example, if the direction is "normal to the surface" then the normal vector is calculated for each selected vertex.

Figure 6:
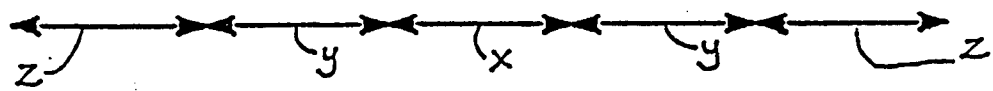
Figure 6A:
Figure 6B:
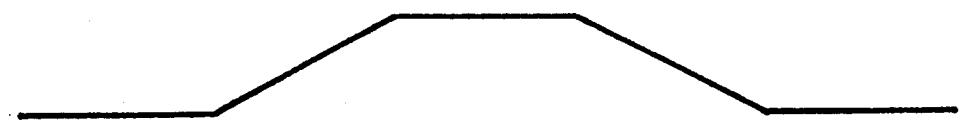
Figure 6C:
Figure 6D:

Referring to FIGS. 6 and 7, a blending range is a group of vertices surrounding the selected vertices. The blending range attenuates the effect of the vertex movement to prevent the creation of abrupt edges between moved and unmoved vertices. The blending range is specified through the UIF. The blending range can be any connected group of vertices which surround the selected vertices. The current implementation of the invention specifies the blending range as real numbers representing the maximum distance between a vertex in the blending range and the nearest selected vertex.

The blending shape defines how a modification is blended into the surrounding surface. The distance by which each vertex in the blending range is moved is based on how far that vertex is from the nearest selected vertex. Vertices nearest to a selected vertex are moved nearly as far as the selected vertices. Vertices furthest from any selected vertex are moved very little. The exact shape of the blending range is called the blending shape. The blending shape is specified through the UIF and can be any formula which maps the distance from the nearest selected vertex into a "position value" between zero (0.0) and one (1.0). Vertices in the blending range which are nearest to a selected vertex have position values nearest to 1.0. Vertices in the blending range which are furthest from any selected vertex have position values nearest to 0.0. The blending shape is specified through the UIF. A flow diagram of blending of a modification procedure is shown in FIG. 7.

Some common blending shapes are illustrated in FIG. 6. Different blending shapes are used for different modifications. A two dimensional cross section of a modification area is illustrated in a) of FIG. 6 before a modification is applied. The cross section is a straight line for purposes of illustration. The region of selected vertices is in the centre (x). Either side of it is the blending range (y,y). Either side of the blending range are two surrounding areas (z,z) which are not effected by this particular modification. The effect of moving the same region of selected vertices by the same amount is illustrated in FIGS. 6b to 6e for various blending shapes as follows:

6a—abrupt edge
6c—ramp
6d—round
6e—cusp

The algorithms and formulas used by the CAD system are presented in below. These include:
Converting the DDF to the. DS;
Interpolation of VOID points;
Vertex selection (rectangle, line, corner);
Drawing the object;
Flood traversal;
Determining the blending range;
Calculating position values;
Moving vertices; and
Converting the DS back into a DDF;

In converting the DDF to the DS, the Digital Data File (DDF) is read by the UIF and converted to the DS. The exact nature of this conversion depends on the format of the DDF. In the current implementation, the digitizing system stores the vertex positions in cylindrical coordinates.

Referring to FIG. 8, it can be seen that a point (A) is specified in cylindrical coordinates by three numbers, namely latitude (B), longitude (C) and radius (D); latitude being the distance along a vertical axis (E), longitude (C) being the angle around the vertical axis (E), and radius (D) being the distance away from the vertical axis (E). In other words, the cylindrical coordinates are expressed relative to a vertical axis and hate the form (lat, long, rad), where:

lat defines the horizontal plane (latitude);
long defines the angular rotation about the axis (longitude); and
rad defines the distance from the axis (radius). For example, all coordinates which lie on a perfect cylinder have the same rad coordinate.

In the current implementation the DDF contains a 2D array of integers. One dimension of the array represents latitudes at fixed vertical separations. The other dimension represents longitudes at fixed angular separations. Each integer stored in the array represents the radius value for the corresponding latitude and longitude.

The DS stores the position of each vertex as a 3D cartesian (xyz) coordinate. The conversion between cylindrical coordinates and cartesian coordinates is accomplished with the following formulas:

$$x = sine(longitude) * radius$$

$$z = cosine(longitude) * radius$$

$$y = latitude$$

As described above the markings made by the prosthetist on the stocking results in gaps or VOID points in the collected coordinate data. Furthermore, other factors also cause such VOID points. Thus there will not necessarily be a valid data point for each (lat,long) position in the DDF. Such positions contain a special value representing a VOID or empty value. This occurs when the laser light is not reflected into the digital camera for one of three reasons:
1) this latitude is above or below the object;
2) the laser light intersected a feature marking made by the prosthetist; or
3) the laser light was scattered due to surface texture VOID points of type (1) are left VOID and in the DS. VOID points of types (2) and (3) are assigned values by interpolating the values of neighboring non-VOID points.

The interpolation algorithm searches for the first non-VOID points in each of 8 directions: up, down, left, right, and the 4 diagonals. Next the distance between each pair of first points is calculated: i.e. the distance between the first points to the right and to the left, between the first points above and below, and between the two pairs of first diagonal points. The pair of first points which are nearest to each other are interpolated to find a value for the VOID point.

For example, referring to FIG. 9, which shows an interpolation of VOID points. Most of the points surrounding the point being interpolated are also void. The first non-VOID point (p) in each of 8 directions are marked. The nearest opposite pair of non-VOID points (p) are marked p1 and p2. The new point value (Pn) is calculated by a weighted interpolation of the pair of nearest points p1 and p2 with the equation:

$$Pn = (n1/(n1+n2)) * p1 + n2/(n1+n2) * p2$$

where
n1 is the number of latitudes or longitudes from Pnew and p1; and
n2 is the number of latitudes or longitudes from Pnew and p2.

Interpolated points are drawn in a different colour than digitized points so the prosthetist can locate the feature marks designating the critical areas on the DS.

In vertex selection (rectangle, line, corner), vertices are selected in the DS by setting the binary flag called selected appropriately (TRUE for selected vertices, FALSE for others). Referring again to FIG. 5, rectangles of Vertices are selected by specifying two vertices (r1,c1) and (r2,c2) representing the lower-left and upper-right corners of the rectangle. The algorithm to select all vertices in the rectangle is as follows:
for each column from c1 to c2
for each row from r1 to r2 set the selected flag to the appropriate value.
This algorithm is used to select rectangular areas for modifications as well as single rows or columns of vertices. It is also used to un-select all vertices in the DS by specifying the two extreme vertices in the DS and setting the selected flags to FALSE.

Lines of vertices are specified by two vertices representing the start and end points of the line. A line of vertices between point (r1,c1) and (r2,c2) is selected With the following algorithm:
increment = (r2−r1)/(c2−c1);
row = r1;
for each column from c1 to c2 set the vertex at row and column appropriately row = row + increment.
This algorithm works best if (r2−r1) is less than (c2−c1). A generalization of this algorithm will also work when this is not the case.

The corners of rectangles are rounded by unselecting a crescent shaped region. The following algorithm is used to select (or un-select) a lower-right corner starting above (r,c), ending left of (r,c), having radius rad.
set (r1,c1) to the first point on row r left of (r,c) and more distant than rad from (r,c) (ie. the starting point),
set (r2,c2) to the first point on col c above (r,c) and more distant than rad from (r,c) (ie. the ending point),
span = c2−c1
for each column from c1 to c2 i = current column−c1, and length = square root of (span*span −i*i) for each row from r1 to (r2−length) mark vertex at row and column appropriately.
This algorithm works for selecting a lower-right hand corner. A generalization of this algorithm works for any of the 4 corners.

In drawing or displaying the object represented by the DS three operations are required as follows:
transform the object from modeling coordinates into viewing coordinates,
project the object from viewing coordinates into screen coordinates, and
draw a 2D line in the graphics viewport between each pair of adjacent vertices in the DS.
The first and second steps are applied to each vertex in the DS and the resulting screen coordinates are saved in each vertex record.

The third step is performed last by traversing the entire DS as in "vertex selection—rectangles" above.

A 3D view is specified by 2 points in space, a view-from point (Vf) and a view-to point (Vt). Viewing coordinates are a cartesian coordinate space in which the origin lies at Vt and Vf lies on the Z axis. A set of 3D modeling coordinates, M, is transformed into viewing coordinates, V, as follows:
Subtract Vt from M,
Rotate M about the y axis so that it lies in the plane x=0,
Rotate M about x axis so that it lies on the Z axis A parallel screen projection maps 3D viewing coordinates (Vx,Vy,Vz) into 2D screen coordinates (Sx,Sy). For a screen with dimensions (Dx,Dy) pixels, where pixel (0,0) is in the lower-left hand corner, the screen projection is as follows:

$$Sx = (Vx + Dx/2) * \text{Scale factor}$$

$$Sy = (Vy + Dy/2) * \text{Scale factor}$$

The value Scale factor will determine how large the image appears on the screen.

Several algorithms in the CAD system make use of a technique called a "flood traversal". FIG. 10 illustrates an example flood traversal and FIG. 11 shows a flow diagram of a general flood traversal.

The flood traversal technique is an efficient technique for processing a region of connected vertices without having to traverse the entire data structure. First a seed vertex $p_v$ (FIG. 10) is processed, then each of its neighboring vertices, or first ring of vertices $p_f$ is processed, then each of their neighboring vertices, or second ring of vertices $P_s$ is processed, and so on. Before each vertex is processed it is checked to see if it is outside the connected region of vertices or if it has already been processed. If either of these conditions is true then it is not processed and the flood traversal does not process its neighbors.

Starting With a seed vertex, the DS is traversed by flooding outward from it. After performing whatever computation is required for the seed vertex, the 4 vertices immediately adjacent to it are considered. The same computation is performed for each of these four and then each of their adjacent vertices are considered. As each vertex is processed, its vertex record is marked "processed". Before each vertex is processed it is checked to establish if it has already been processed. If it has, then it is not processed and neither are any of its adjacent vertices.

Flood traversals are used in the following algorithms:
determining the blending range,
selecting and un-selecting vertices and clearing the blending range,
moving and un-moving selected vertices, and
converting the DS back into a DDF.

Before the selected vertices are moved, the blending range surrounding them is determined. This algorithm assumes that the selected vertices and their blending range combine to form one contiguous region of the DS. The range is determined using a flood traversal starting with a seed vertex, Vs, which is know to be a selected vertex. FIG. 7 is a flow diagram of the following algorithm:
if this vertex has already been visited during this traversal then stop
mark this vertex processed;
if this vertex is selected
mark it in range,
set its position value to 1.0, otherwise
calculate the distance to the nearest selected Vertex;
if the distance is greater than range then stop, otherwise
mark it in range,
calculate its position value; repeat the algorithm for each adjacent vertex.

In calculating position values, the position value of each vertex in the blending range is based on the distance D to the nearest selected vertex, the range R, and on the blending shape selected. The formulas used for four blending shapes are listed below.

| Blending Shape | Position Value |
| --- | --- |
| Abrupt Edge | 1.0 |
| Ramp | 1.0 − D / Range |
| Cusp | 1.0 − (D * D) / (Range * Range) |
| Round | 1.0 − (cosine(D / Range * PI) * −0.5) + 0.5; |

In moving vertices, a flood traversal is used to move the selected vertices and the blending range surrounding them. Starting with a selected vertex, each vertex which is marked in range (including the selected vertices) is processed. Selected vertices are moved by the displacement specified by the UIF. For each vertex in the blending range, the displacement is first scaled by that vertex's position value (between 0 and 1), then the vertex is moved by the scaled displacement. The direction in which each vertex is moved is specified by the UIF. In most cases vertices are moved along a line which is normal to the surface of the object at that vertex. The surface normal of the object at vertex V is calculated as the average of the 4 cross products:
V Vup cross V Vright
V Vright cross V Vdown
V Vdown cross V Vleft
V Vleft cross V Vup
where Vup, Vright, Vdown, and Vleft are the vertices adjacent to V.

Referring now to the process of converting the DS back into a DDF, after the DS has been modified, it is written to a new DDF.. First it is converted from cartesian coordinates back into cylindrical coordinates A value must be found on the surface of the object for each (latitude,longitude) coordinate. Most vertices of the DS no longer align exactly with the fixed latitudes or longitudes because they have been moved. Therefore, this algorithm involves intersecting a 3D ray representing each (lat,long) coordinate with the surface of the object in the DS.

A description will now be given of the process of converting DS to DDF. As can be seen in FIG. 12, the vertices of the modified data structure (DS) for the modified object M are no longer aligned with the cylindrical coordinate space. A surface of triangles T is constructed on the DS object. An imaginary ray is constructed for every (latitude, longitude) coordinate in cylindrical coordinate space and is intersected with the surface of the modified object. The new radius value is calculated as the distance from the vertical axis to the intersection point.

A high level description of the algorithm follows:
for each fixed latitude in the cylindrical coordinate space, for each fixed longitude in the cylindrical coordinate space construct a 3D ray emanating from the cylindrical axis, and
intersect the ray with the object in the DS,
calculated the cylindrical radius to the intersection point, and
save the radius value in the DDF.

In order to intersect rays with the DS two triangles are constructed for each vertex V:
Vup V Vright, and
Vdown V Vleft.

Each ray will intersect exactly one triangle. The correct triangle is found by a flood traversal starting with those triangles which are constructed from a seed vertex. If they do not intersect the ray, then the triangles formed from adjacent vertices are tried, and so on. The seed vertex is the one which was originally converted from the current (lat,long) coord when the DS was built.

Intersecting the imaginary rays with triangles on the object is a two step process. The first step is to find the point of intersection, p, between the ray and the plane of the 3D triangle (v1, v2, v3) (FIG. 13). The second step is to determine whether p lies within the triangle.

The intersection point P between ray (r1 r2) and the plane containing points v1, v2, v3 is calculated as follows:

$$N = (v2 - v1) \text{ cross } (v3 - v1)$$

$$D = (r2 - r1) \text{ dot } N$$

$$t = -(Nx * r1x + Ny * r1y + Nz * r1z)/D;$$

$$P = r1 + (r2 - r1) * t$$

Determining whether P lies within the 3D triangle is done by projecting the vertices of the triangle and p onto an axis-orthogonal plane (e.g. the plant Y=0) shown in FIG. 13 and comparing them in two dimensions.

In 2D, a point p lies within a triangle (v1, v2, v3) if the following three formulas all evaluate to a positive number:

$$(v2 - v1) \text{ cross } (p - v1)$$

$$(v3 - v2) \text{ cross } (p - v2)$$

$$(v1 - v3) \text{ cross } (p - v3)$$

Although reference is made throughout the above description to the production of a socket for a prosthetic structure, it is apparent that a system and process similar to the described specific embodiment of the present invention is equally applicable for use in producing the seating of orthotics and such devices.

Various other modifications to the specific embodiment which has been set forth as an example will be apparent to those skilled in the art without departing from the spirit of the invention as defined with the accompanying claims.

We claim:

1. A method of producing a structure for use in a prosthetic, orthotic having an inner surface for engagement with a portion of a human body comprising scanning said body portion with a laser digitizer to produce a plurality of contour coordinates representing an outer contour of said body portion along a plurality of closely spaced lines read by said laser digitizer, storing said contour coordinates representing a digital image of the contour of said body portion, generating a code from said digital image for controlling a cutting machine to produce a mold having an outer surface contoured in a shape of said body portion, and producing said structure from said mold, the improvement which takes into consideration loading effects on said body portion is characterized by:
   a) encasing and loading said body portion in a flexible support having a reflective outer surface for laser digitizing;
   b) inspecting said encased and loaded body portion and locating load bearing and non-load bearing, basic modification sites thereon;
   c) identifying said basic modification sites and discrete modification sites within said basic modification sites by means of a series of small, non-reflecting markings on said reflective surface;
   d) displaying said digital image of said contour graphically and identifying said discrete and basic modification sites as void-points produced by said non-reflecting markings;
   e) producing a modified digital image by selectively adjusting certain discrete modification sites within said basic modification sites positively to produce enlargements and adjusting discrete modification sites in other selected basic modification sites negatively to produce reductions;
   f) producing said mold from said modified data having a surface contoured in the shape of said body surface but including areas of enlargements and reductions; and
   g) producing said structure from said mold whereby the areas of enlargement correspond to non-load bearing basic modification sites and areas of reduction correspond to load bearing basic modification sites.

2. The method as defined in claim 1, wherein said body portion is confined in a material assuming the outer contour of the body portion and providing a laser reflective outer surface.

3. The method as defined in claim 2, wherein each critical areas is defined by a series of dots forming the non-reflective markings.

4. The method as defined in claim 3, wherein said series of dots are located about the periphery of the critical area.

5. The method as defined in claim 3, wherein one of said critical areas is a bony prominence, and the apex of the prominence is marked with at least one of said dots.

6. The method as defined in claim 5, wherein all the selected vertices in each basic modification area are moved in the same direction by the same amount.

7. The method as defined in claim 6, wherein said selected vertices are established by identifying a region of connected vertices, and including the step of moving said selected vertices by using flood transversal.

8. The method as defined in claim 7, wherein said flood transversal includes the steps of selecting a seed vertex within said region and carrying out a process of computations for accomplishing the desired movement of said seed vertex, processing each neighboring vertex in a first ring outwardly of said seed vertex in a like manner, and continuing to process in a like manner each successive ring outwardly from said seed vertex until all vertices within said region are processed.

9. The method as defined in claim 2, wherein the material is stretchable stocking.

10. The method as defined in claim 9, wherein said body portion is a residual leg portion of a patient, said method further including the steps of locating the patient on a horizontal platform provided with an opening, attaching said stocking with an upper peripheral opening thereof affixed within the opening of said platform, locating said residual leg portion in said stocking and positioning said patient to support a significant portion of the patient's weight by way of the residual limb within said stocking.

11. The method as defined in claim 1, wherein at least some of the selected vertices of at least one basic modification area are 11 moved in the same direction by the same amount.

12. The method as defined in claim 11, wherein a blend range is provided at a periphery of at least one of the basic modification areas, whereby sharp edges at said periphery between the enlargements or reductions and the surrounding surface of the structure are avoided.

13. The method as defined in claim 12, wherein vertices in said blend range surrounding said one basic modification area are identified, and further including the step of moving each identified vertex in the blend area in the same positive or negative direction as the selected vertices for said one basic modification area, the distance of movement of each vertex in the blend area varying depending on the distance of the vertices from said one modification area.

14. The method as defined in claim 13, wherein said laser digitizer includes a laser camera mounted for 360° movement about said longitudinal axis of said leg portion, and including the steps of indexing said camera a fraction of a degree at a time through the 360° movement for producing said plurality of contour coordinates.

15. The method as defined in claim 12, wherein the longitudinal axis of said leg portion supported in said stocking is substantially vertical.

16. The method as defined in claim 1, and further including the steps of using a digitizer control program for controlling the scanning of said body portion and for producing and storing said contour coordinates;

using a specially developed CAD system program for producing said modified data;

using a specially developed program for converting said modified data to produce a G code; and using a G code transmission program for utilizing the produced G code to control said cutting machine.

17. The method as defined in claim 16, and wherein the step of storing said contour coordinates includes collecting digital data in a Digital Data File.

18. The method as defined in claim 17, and wherein the step of graphically displaying includes reading the Digital Data File by way of a User Interface, and storing said digital data in a Data Structure wherein said Data Structure contains said contour coordinates in the form of a plurality of vertices.

19. The method as defined in claim 18, wherein said User Interface provides a window display showing the Data Structure by a wire frame view formed by a line connected between each vertex and each immediate neighbor vertex above and below and to the left and to the right of said each vertex.

20. The method as defined in claim 18, and further including the step of converting said contour coordinates of said Data Structure from three-dimensional (3D) to a two-dimensional (2D) display screen at a workstation.

21. The method as defined in claim 18, wherein said CAD system stores information contained in said Digital Data File in a special Data Structure representing each coordinate with a vertex record.

22. The method as defined in claim 21, wherein the vertex records are stored in a two-dimensional array.

23. The method as defined in claim 18, wherein a direction for moving said vertices is expressed in terms normal to the surface represented by said Data Structure.

24. The method as defined in claim 18, wherein the contour coordinates produced by said digitizer control program are stored as vertices identified in cylindrical coordinates.

25. The method as defined in claim 24, wherein the Data Structure stores the position of each vertex in 3D cartesian coordinates.

26. The method as defined in claim 25, wherein said Data Structure as modified is written to a new Digital Data File.

27. The method as defined in claim 26, wherein said Data Structure is converted from cartesian coordinates back into cylindrical coordinates prior to being written into a new Digital Data File.

28. The method as defined in claim 18, wherein said VOID-points are assigned values in said Data Structure.

29. The method as defined in claim 28, wherein said VOID-points are analyzed by interpolation using values of neighboring non-VOID-points, and a new point value is assigned to the VOID-point.

30. The method as defined in claim 29, wherein said new point is calculated by a weighted interpolation of a pair of non-VOID-points nearest said VOID-points.

31. The method as defined in claim 29 or 30, wherein the new points are shown on a two-dimensional display screen at a workstation, said new points being shown as a colour different than the other non-VOID-points on said display screen.

32. The method as defined in claim 16 and further comprising the steps of using said specially developed CAD program for uniformly reducing, by a preselected percentage, the volume of the digital image represented by said contour coordinates.

33. The method as defined in claim 16, and further comprising the step of using said specially developed CAD program for providing a uniform shrink about a peripheral portion of the digital image represented by said contour coordinates.

34. The method as defined in claim 16, wherein said specially developed CAD system program provides a colour coding capability, and including the steps of displaying an unmodified body portion in one colour and superimposing thereon a configuration representative of the modified data in a different colour.

35. The method as defined in claim 16 wherein the producing of the modified data includes the steps of selecting a set of vertices to move and specifying a distance and a three-dimensional direction for movement.

36. The method as defined in claim 16, wherein the producing of the modified data includes the steps of separately specifying and altering a set of parameters for each modification area.

37. The method as defined in claim 16, wherein vertices are selected graphically using a 2D pointing device through a User Interface.

38. The method as defined in claim 1, further comprising the steps of maintaining the modified data subsequent to producing said structure, and using the maintained data at a later time for producing further modified data and thereafter producing a refit structure.

* * * * *